(12) United States Patent
Fox (10) Patent No.: US 10,967,136 B2
(45) Date of Patent: Apr. 6, 2021

(54) PAIN-AVERTING DEVICE (PAD)

(71) Applicant: Felisha Fox, St. Louis Park, MN (US)

(72) Inventor: Felisha Fox, St. Louis Park, MN (US)

(73) Assignee: Felisha V. Fox, Minneapolis, MN (US)

( * ) Notice: Subject to any disclaimer, the term of this patent is extended or adjusted under 35 U.S.C. 154(b) by 326 days.

(21) Appl. No.: 16/235,948

(22) Filed: Dec. 28, 2018

(65) Prior Publication Data
US 2020/0206437 A1   Jul. 2, 2020

(51) Int. Cl.
*A61M 5/42* (2006.01)
*H02J 7/00* (2006.01)

(52) U.S. Cl.
CPC ........... *A61M 5/422* (2013.01); *H02J 7/0013* (2013.01); *A61M 2205/582* (2013.01); *A61M 2205/8206* (2013.01); *A61M 2205/8237* (2013.01)

(58) Field of Classification Search
CPC ........... A61M 5/422; A61M 2205/582; A61M 2205/8206; A61M 2205/8237; A61M 5/178; A61M 2005/1787; H02J 7/0013; A61C 19/08; A61C 1/081; A61B 5/150053; A61B 5/150106
USPC ............................... 604/112, 93.01, 187, 191
See application file for complete search history.

(56) References Cited

U.S. PATENT DOCUMENTS

| | | | |
|---|---|---|---|
| 2,674,246 A * | 4/1954 | Bower | A61M 5/422 604/198 |
| 3,620,209 A * | 11/1971 | Kravitz | A61M 5/422 601/79 |
| 4,373,526 A * | 2/1983 | Kling | A61M 5/422 604/117 |
| 5,647,851 A | 7/1997 | Pokras | |
| 6,231,531 B1 * | 5/2001 | Lum | A61H 23/0263 600/573 |
| 8,660,652 B2 | 2/2014 | Vallero | |
| 9,289,323 B2 | 3/2016 | Marton | |
| 9,439,829 B2 | 9/2016 | Lee | |
| 9,770,561 B1 * | 9/2017 | Dixon | A61B 5/150106 |
| 2003/0040714 A1 * | 2/2003 | Coss | A61M 5/3287 604/187 |
| 2005/0182364 A1 * | 8/2005 | Burchman | A61M 5/422 604/112 |
| 2008/0086063 A1 * | 4/2008 | Baxter | A61F 7/10 601/46 |
| 2008/0086159 A1 * | 4/2008 | Zweifler | A61C 1/081 606/185 |
| 2008/0086187 A1 | 4/2008 | Baxter | |
| 2008/0188779 A1 * | 8/2008 | Vallero | A61N 1/0492 601/21 |
| 2008/0255483 A1 * | 10/2008 | Goldberg | A61H 23/02 601/72 |

(Continued)

*Primary Examiner* — Justin M Jonaitis (57) ABSTRACT

An injection apparatus includes a base, an anesthetic holder, one or more vibration motors, and a hollow cylinder. The base includes a bottom surface for placement against a patient's skin, wherein the base includes one or more apertures. The anesthetic holder extends from the base and retains an anesthetic, wherein the holder is in fluid communication with the one or more apertures located on the base. The one or more vibration motors are affixed to the holder. The hollow cylinder includes a first end and a second end, wherein the first end is configured to receive an injecting pen and the second end is located adjacent to the base and is configured to allow the injecting pen to contact the patient's skin.

3 Claims, 8 Drawing Sheets

(56) References Cited

U.S. PATENT DOCUMENTS

| | | |
|---|---|---|
| 2010/0179457 A1 | 7/2010 | Blaine |
| 2010/0211010 A1* | 8/2010 | Wycoki ................ A61M 5/422 |
| | | 604/112 |
| 2010/0274162 A1 | 10/2010 | Evans |
| 2011/0046556 A1* | 2/2011 | Kraft ................ A61M 37/0015 |
| | | 604/173 |
| 2011/0166498 A1 | 7/2011 | Shantha |
| 2014/0074080 A1* | 3/2014 | Halaka ............ A61B 5/150022 |
| | | 606/16 |
| 2014/0206947 A1 | 7/2014 | Isserow |
| 2015/0250413 A1 | 9/2015 | Redwood |
| 2015/0283334 A1* | 10/2015 | Marx ................ A61M 5/3287 |
| | | 604/112 |
| 2016/0030685 A1 | 2/2016 | Lane |
| 2018/0071457 A1* | 3/2018 | Lima ................ A61M 5/2053 |

\* cited by examiner

PAIN-AVERTING DEVICE (PAD)

BACKGROUND

Field of Invention

The present invention relates to devices for administering injections to patients and more particularly to a device that reduces pain and fear associated with injections.

Currently, around 300,000 children in the United States have been diagnosed with Juvenile Arthritis (JA). The main source of treatment for these children is taking an injection, this is also true for many other conditions. Whether this injection is monthly, weekly, or daily, it is a challenge for children to be comfortable with them.

If there was an easier way for children and adults to take their injections, not only arthritis patients, others as well, it could eliminate the fear and hesitation they have towards them. Current options do not eliminate both the fear component and the pain component most children and adults face with their injections.

SUMMARY

According to some aspects, a device includes a holder configured to receive an injector. The holder is configured to retain a vibrator and a receptacle for retaining and dispensing an anesthetic.

DETAILED DESCRIPTION

Drawings—Reference Numerals

Figure 1:
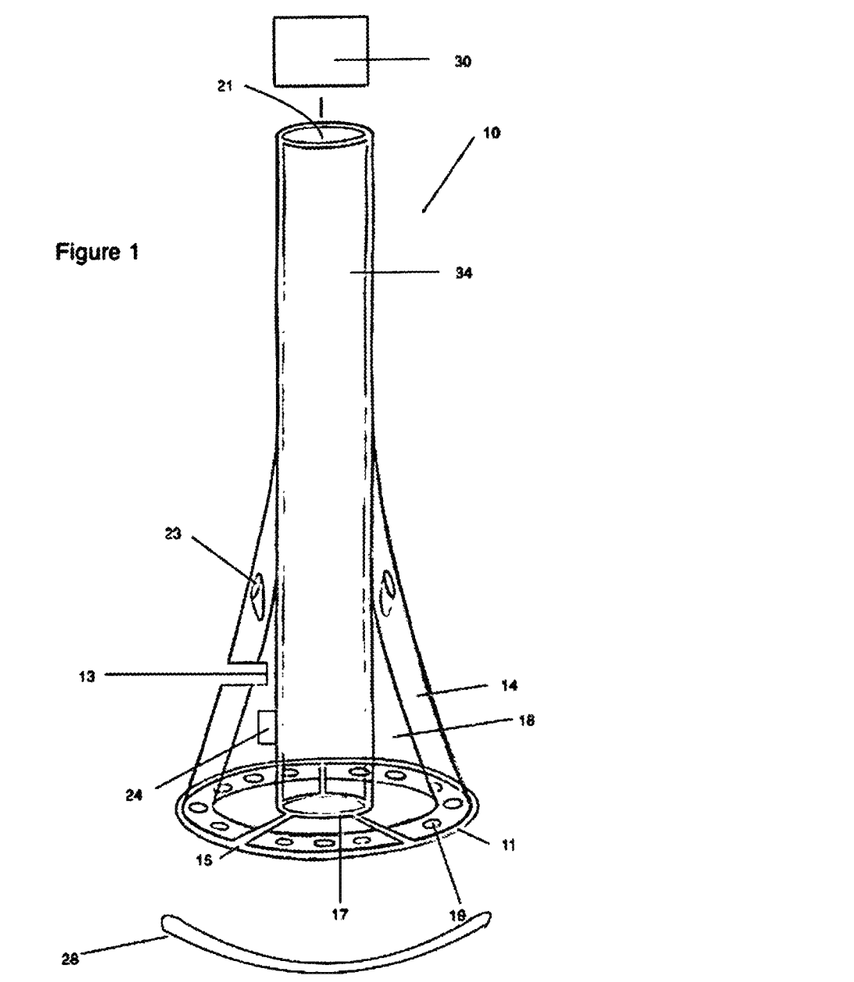
FIG. 1 is a perspective view of the device according to some embodiments.

10 Device
11 Base
13 Micro USB charging port
14 Holder for anesthetics
15 Outer radius portion
17 Inner radius portion
18 Holder for electrical components
19 Apertures
20 Battery
21 Opening for injection pen
22 Charger
23 Opening(s) to add anesthetic
24 Vibration Motors
26 Turn on/off mechanism
28 Cap
30 Injecting pen
32 Viewing window
34 Cylindrical tube
36 Click on mechanism
38 Click in component
40 Immunization gun
42 Anesthetic FIG. 1 is a perspective view of the device 10 according to some embodiments. In some embodiments of FIG. 1, the device includes a base 11, Micro USB charging port 13 to recharge device 10, an anesthetics holder 14, an outer radius portion 15, an inner radius portion 17, apertures 19, opening for injection pen 21 where the injecting pen 30 will be placed, opening(s) to add anesthetic 23, vibration motors 24, cylindrical tube 34, and a cap 28. In the embodiment shown in FIG. 1 the vibration motors 24 are attached to the cylindrical tube 34. Having the vibration motors 24 attached to the cylindrical tube 34 allows for the vibration to be closest to the injecting pen 30 which is placed inside the cylindrical tube 34. This is beneficial because the vibration will be close to the injection site.

In some embodiments, a cylindrical tube 34 extends from the inner radius portion 17 in a direction perpendicular to the base 11. The injecting pen 30 will be inserted into the cylindrical tube 34 through the inner radius portion 17. In some embodiments the Micro USB charging port 13 is located on the outer portion of the holder for electrical components 18. In some embodiments the holder for anesthetics 14 will be detachable. The injecting pen 30 will be inserted into the device 10, but not included in with the device. The anesthetic 42 will be inserted into the device 10, once the device is ready to be used, but not beforehand. The anesthetic 42 inserted into the device 10 will have the cooling effect without having to place an icepack on the patient's skin. The holder for anesthetics 14 will be refillable and have an opening(s) to add anesthetic 23 that will be able to be removed from the holder for electrical components 18 of the device 10 and the cylindrical tube 34 that holds the injection pen 30. It will be able to be removed in order to be cleaned and refilled as needed. These compartments will be dishwasher safe. The holder for anesthetics 14 will either be a click and release or some sort of magnetic release to remove from the rest of the device 10 (i.e. holder for electrical components 18 and cylindrical tube 34).

This device 10 has many new and innovative ways in order to reduce pain and anxiety for a patient during the time of an injection. The manner of this device 10 is holding anesthetics 14 and holding electrical components 18 that will be applied to the surface of the skin at an injection site. Assembly of the device includes connecting all components. Fill holders for anesthetics 14 and make sure cap 28 is removed. Slide the injecting pen 30 into cylindrical tube 34. The Switch 26 will be turned on and start the vibration from the Vibration Motors 24. The Battery 20 will be providing electricity to the Vibration Motors 24. The anesthetic 42 will seep through the apertures 19 in the base 11 and will be applied to the skin through apertures 19. The Vibration Motors 24 will be operating. The user will to turn on the device and place injecting pen 30 into the cylindrical tube 34. Once injection is complete, user takes out injecting pen 30 and the Vibration Motors 24 will shut off. The user may place the cap on the device 28 to keep the anesthetic from being expelled. The Battery can be charged 22 through the Micro USB port 13. The device 10 may then be dismantled if user chooses to do so.

The combination of both anesthetics 42 and vibration motors 24 will make it so the patient can take an injection with less pain, since taking the injection as often as they do can be a burden in itself. The vibration motors 24 allow the pain from the actual needle to be much less while the anesthetic 42—rather than ice—does not damage the skin of the patient and also to make the pain of the chemical reaction from the medication much less. The final component of the device is the tube that covers the actual injection pen 30. The injection pen will slide into this cylindrical tube 34 that will lessen the anxiety of the child due to the fact that they don't have to see their injection pen 30. Fear is a big component of making the injection painful and a burden, by hiding the injection pen 30 itself behind some sort of positive image, patients might not be as scared of their injections and the pain and fear will be lessened. The cylindrical tube 34 will be in the center and be surrounded by the holder for electrical components 18 and the holder for anesthetics 14. Having these three innovative components, vibration motors 24, anesthetics 42, and cylindrical tube 34 to hide injection pen, work as one during the time of an injection can do a lot of good for many patients who have to take injections on a regular. The design of the device 10 will also be smooth and symmetrical to give off a clean and calming look. An alternate embodiment of this device for veterinary purposes, illustrated in FIG. 1A which shows the side view of device 10, will not include the top portion of the cylindrical tube 34 and the viewing window 32. Instead it may contain a click on mechanism 36 to attach to immunization gun through click on component 38 for animal immunizations or injections. All holders for electronic components 18 and holders for anesthetics 14 may be the same. The click on mechanism 36 may mount to a variety of different types of injections. The immunization guns 40 can be very painful and this device 11 can benefit a lot of animals. The anesthetics 42 and vibration motors 24 will reduce the pain these animals go through.

Figure 2:
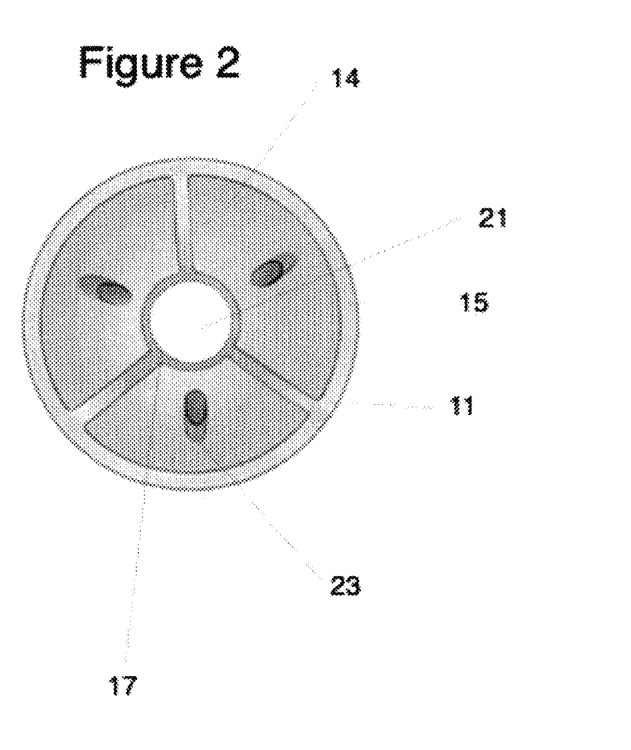
FIG. 2 is a top view of the device according to some embodiments.

FIG. 2 is a top view of device 10 according to some embodiments. In some embodiments of FIG. 2, device 10 shows, the base 11, holder for anesthetics 14, outer radius portion, 15, inner radius portion 17, opening for injection pen 21, and opening(s) to add anesthetic 23. The opening(s) to add anesthetics will be parallel to the cylindrical tube 34.

Figure 3:
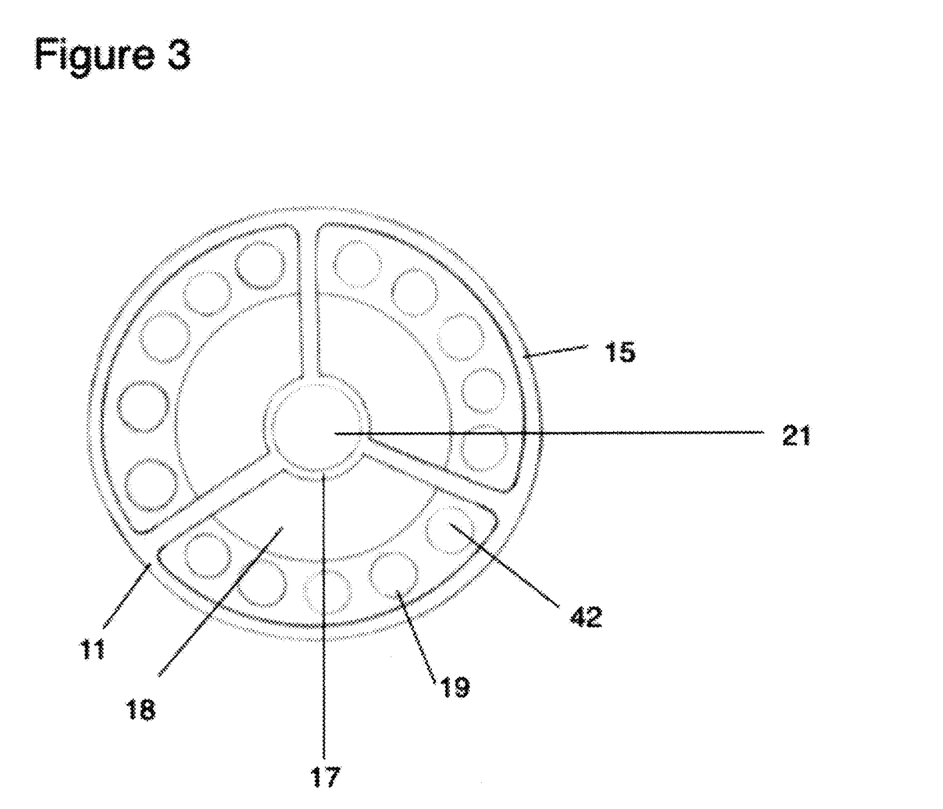
FIG. 3 is a bottom view of the device according to some embodiments.

FIG. 3 is a bottom view of device 10 according to some embodiments. In some embodiments of FIG. 3, it shows the base 11, outer radius portion 15, inner radius portion 17, apertures 19, opening for injection pen 21, and the location of the anesthetic 42. Some embodiments include apertures 19 that are connected on the inside of the outer radius portion 15 of the base 11. These apertures 19 dispense anesthetics 42. The inner radius portion 17 connects to the holder for electrical components 18 and the outer radius portion 15 connects to the holder for anesthetics 14. The inner radius portion 17 also holds the injecting pen 30 through the opening for injection pen 21. The injection pen 30 will be inserted in the cylindrical tube 34 in order to have to most accuracy and effect.

Figure 4:
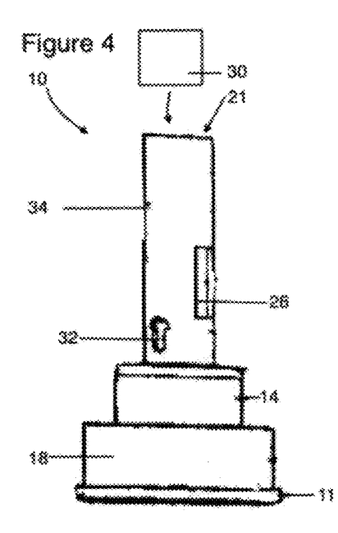
FIG. 4 is a side view of the device according to some embodiments.

FIG. 4 is a prospective view of the device 10 according to some embodiments. In some embodiments of FIG. 4, device 10 shows, the base 11, holder for anesthetics 14, holder for electrical components 18, opening for injection pen 21, turn on/off mechanism 26, injection pen 30, viewing window 32, and the cylindrical tube 34. In an alternative embodiment the holder for electrical components 18 will be attached to the outer radius portion 15 and the holder for anesthetics will be attached to the inner radius portion 17. This view shows the viewing window 32 to view medication, this window is located on the side of the cylindrical tube 34.

Figures 5, 6:
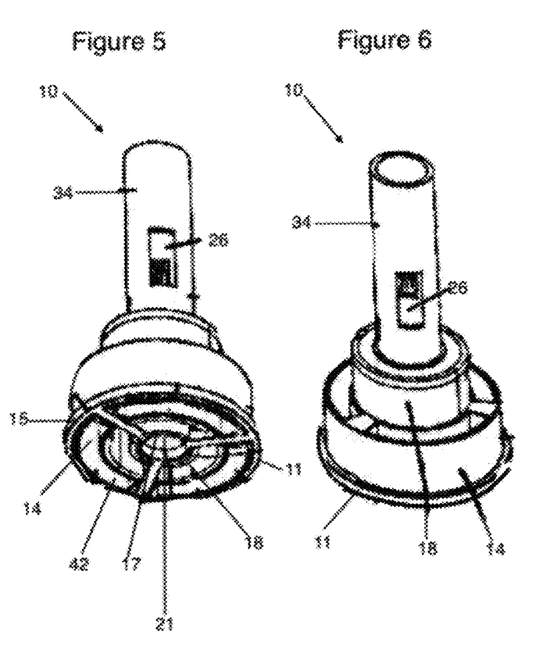
FIG. 5 is a bottom perspective view of the device according to some embodiments.
FIG. 6 is a top perspective view of the device according to some embodiments.

FIG. 5 shows a bottom isometric view of device 10. In some embodiments of this FIG. 5, it the base 11, holder for anesthetics 14, outer radius portion 15, inner radius portion 17, holder for electrical components 18, opening for injection pen 21, turn on/off mechanism 26, the cylindrical tube 34, and the location for the anesthetic 42. shows location for turn on/off mechanism 26. In some embodiments of FIG. 5, it shows the holder for the anesthetics 14 without the apertures 19 and without the opening(s) to add anesthetics 23.

FIG. 6 shows a top isometric view of device 10. In some embodiments of FIG. 6 it shows the base 11, holder for anesthetics 14, holder for electrical components 18, turn on/off mechanism 26, and the cylindrical tube 34. In some embodiments of this view it shows the location of the turn on/off mechanism 26. When the device is ready to be used the patient will turn on the device through the turn on/off mechanism 26. The turn on/off mechanism can be anything from a switch, to a button, to a capacity sensor, which senses contact with the skin and turns on. Once the device 10 is finished being used, the patient will shut off the device 10 through the turn on/off mechanism 26 and will be able to recharge that section through a Micro USB charging port 13. The patient will also place the cap over the apertures 19 so they will not leak.

Figure 7:
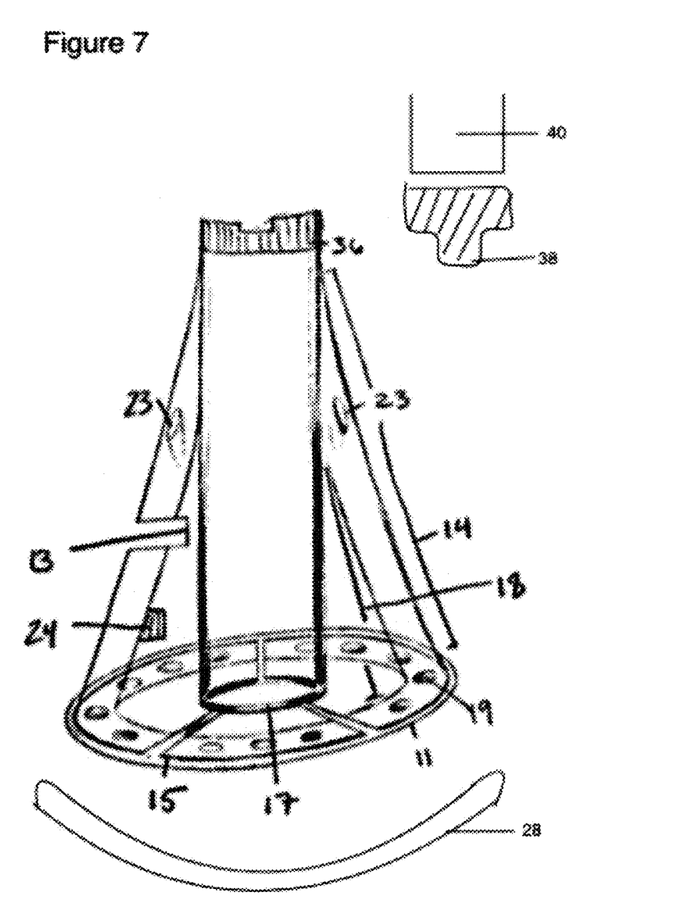
FIG. 7 is a perspective view of the device according to some embodiments.

FIG. 7 is a prospective view of the device according to some embodiments. In some embodiments of FIG. 7 it shows, the cylindrical tube 34 will be replaced with a click on mechanism 36 that will click into a click in component 38 on animal immunization guns 40. The immunization gun 40 will be inserted into the device 10, through the click in component 38, but not included in with the device 10. The anesthetic 42 will be inserted into the device 10, once the device is ready to be used, but not beforehand. This embodiment will be used for veterinary purposes. For this embodiment, instead of sliding injection pen 30 into device, user will click on device to immunization gun 40 or injection pen 30.

Figure 8:
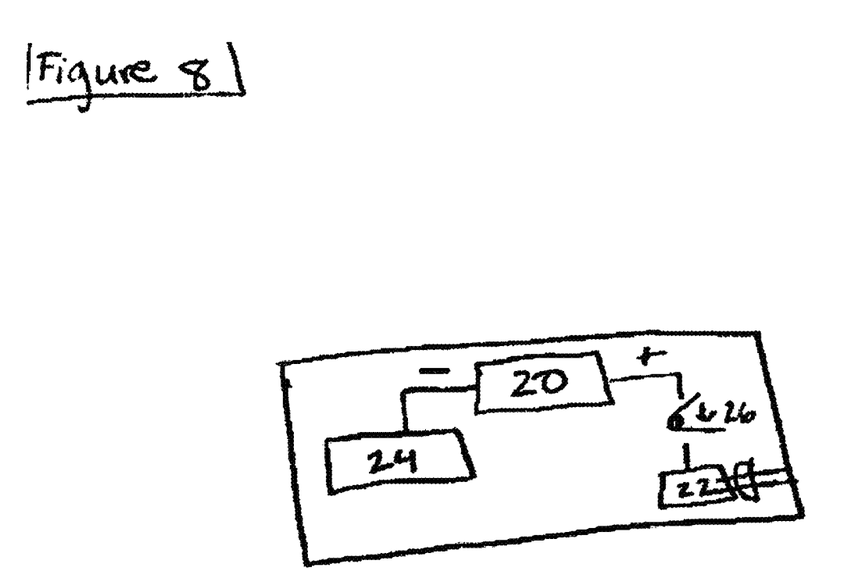
FIG. 8 is an electrical schematic of the electrical components.

FIG. 8 is an electrical schematic of the electrical components. In some embodiments of FIG. 8, it shows the holder for electrical components 18, which includes: battery 20, vibration motors 24, turn on/off mechanism 26, and the Micro USB charging port 13. On the negative end of the Battery 20, there is Vibration Motors 24 that will be placed within the holder for the electrical components 18. On the positive end of the Battery 20, it will connect the turn on/off mechanism 26 and the Charger 22 through the Micro USB charging port 13. The Battery 20 and the Charger 22 will both be placed within the holder for electrical components 18. The turn on/off mechanism 26 will be placed on the outside top portion of cylindrical tube 34. The vibration motors 24 will be engraved in a filler material in order to make sure that the individual vibration motors serve their purpose. The motors 24 will be rechargeable through a micro USB charging port 13 along the side of the device 10. While it is in motion the vibration motors 24 will gain energy from the recharged battery 20 and will be ready for use.

Figure 9:
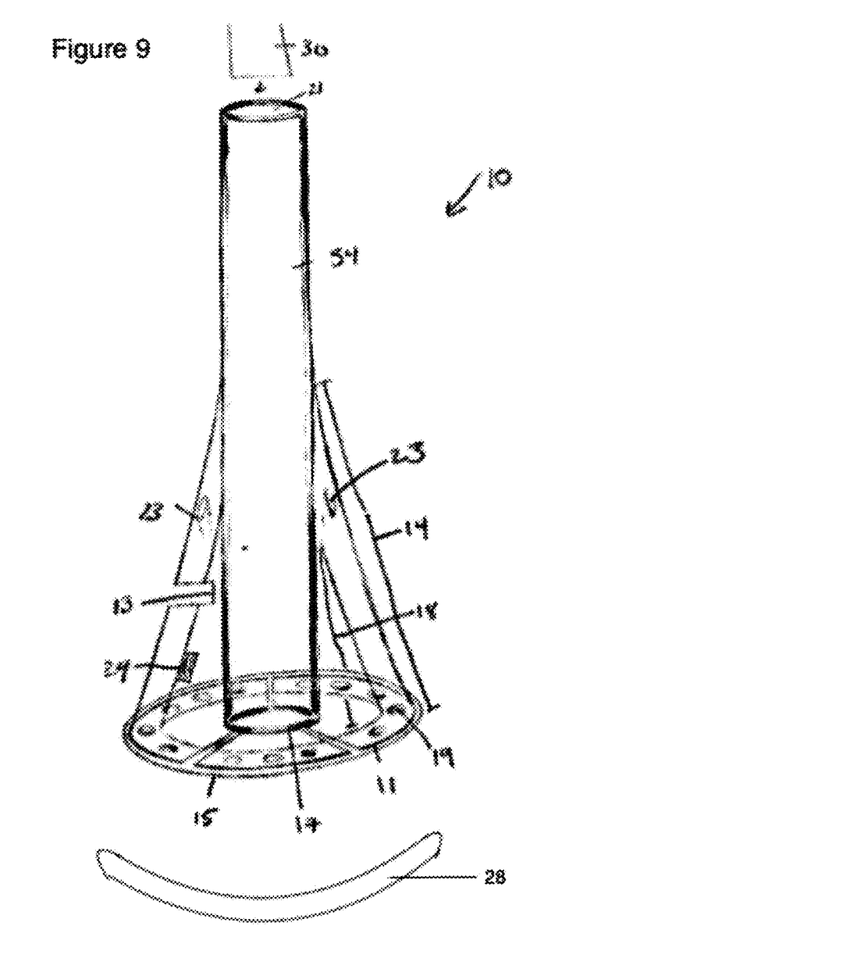
FIG. 9 is a perspective view of the device according to some embodiments.

FIG. 9 is a perspective view of the device according to some embodiments. In some embodiments of FIG. 9, the device includes once again includes a base 11, Micro USB charging port 13 to recharge device 10, the outer radius portion 15, the inner radius portion 17, apertures 19, opening for injection pen 21 where the injecting pen 30 will be placed, opening to add anesthetic 23, vibration motors 24, holder for anesthetics 14, the cap 28, and the cylindrical tube 34. In this embodiment, FIG. 9, the vibration motors 24 are attached to the holder for anesthetics 14. Having the vibration motors 24 attached to the holder for anesthetics 14 allows for the vibration motors 24 to be farther away from the patient's skin.

Figure 10:
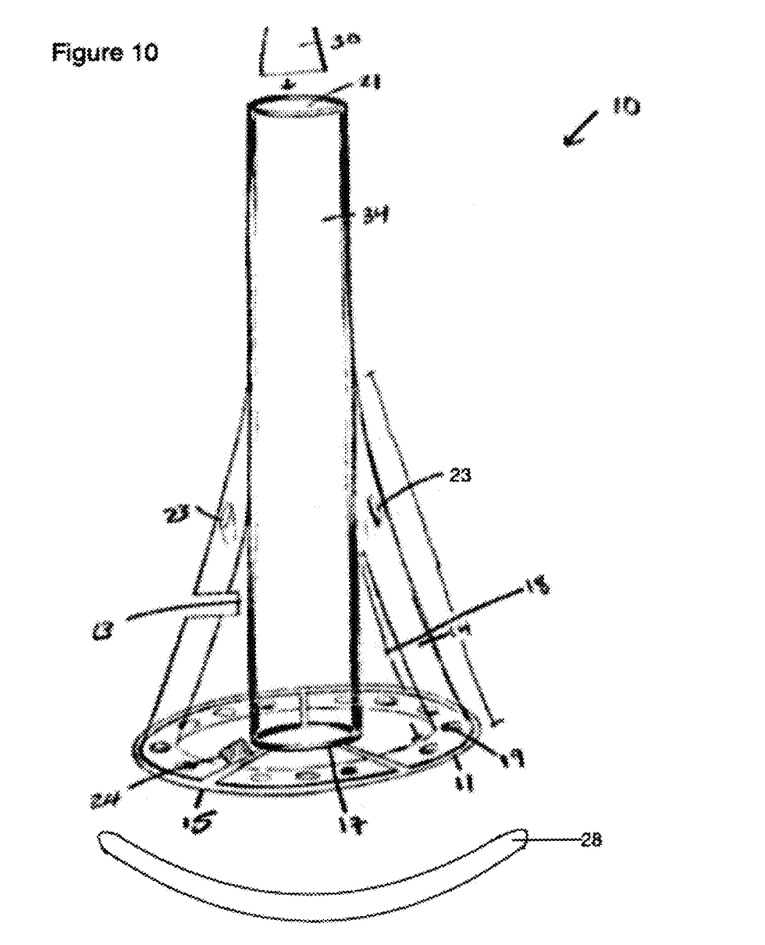
FIG. 10 is a perspective view of the device according to some embodiments.

FIG. 10 is a perspective view of the device 10 according to some embodiments. In some embodiments of FIG. 10, the device includes Micro USB charging port 13 to recharge device 10, the holder for anesthetics 14, the outer radius portion 15, the inner radius portion 17, apertures 19, opening for injection pen 21 where the injecting pen 30 will be placed, opening to add anesthetic 23, vibration motors 24, the base 11, the cap 28, and the cylindrical tube 34. In FIG. 1C the vibration motors 24 will be attached to the base 11. Having the vibration motors 24 attached to the base 11, allows the vibration to be felt with more impact on the patient's skin.

I claim:

1. An injection apparatus comprising:
    a base having a ring shaped bottom surface for placement against a patient's skin, wherein the base includes one or more apertures;
    an anesthetic holder connected to and extending from the base that retains an anesthetic, wherein the holder is in fluid communication with the one or more apertures to dispense the anesthetic to the patient's skin;
    one or more vibration motors affixed to the holder; and
    a hollow cylinder having a first end, a second end, and a longitudinal body extending between said first and second end, wherein an opening in the first end is configured to receive an injecting pen longitudinally within an interior of the hollow cylinder and the second end is located concentrically adjacent to the base and is configured to allow the injecting pen to contact the patient's skin to administer an injection to the patient.

2. The injection apparatus of claim 1, further including a capacitive sensor located on the base and configured to detect contact of the base with the patient's skin to turn the device on.

3. The injection apparatus of claim 1, further including a Universal Serial Bus port electrically connected to the one or more vibration motors and/or one or more batteries for powering/recharging the one or more vibration motors and/or one or more batteries.

* * * * *